United States Patent
Hendriks et al.

(10) Patent No.: US 9,867,599 B2
(45) Date of Patent: Jan. 16, 2018

(54) OPTICAL GUIDED VACUUM ASSISTED BIOPSY DEVICE

(71) Applicant: KONINKLIJKE PHILIPS N.V., Eindhoven (NL)

(72) Inventors: Bernardus Hendrikus Wilhelmus Hendriks, Eindhoven (NL); Christian Reich, Eindhoven (NL); Waltherus Cornelis Jozef Bierhoff, Veldhoven (NL); Manfred Mueller, Eindhoven (NL); Franciscus Marinus Antonius Maria Van Gaal, Heeze (NL); Jozef Christiaan Mathieu Versleegers, Bree (BE); Vishnu Vardhan Pully, Eindhoven (NL); Sven Stoffelen, Ittervoort (NL)

(73) Assignee: Koninklijke Philips N.V., Eindhoven (NL)

( * ) Notice: Subject to any disclaimer, the term of this patent is extended or adjusted under 35 U.S.C. 154(b) by 8 days.

(21) Appl. No.: 14/762,526

(22) PCT Filed: Oct. 16, 2013

(86) PCT No.: PCT/IB2013/059387
§ 371 (c)(1),
(2) Date: Jul. 22, 2015

(87) PCT Pub. No.: WO2014/132110
PCT Pub. Date: Sep. 4, 2014

(65) Prior Publication Data
US 2015/0359525 A1    Dec. 17, 2015

Related U.S. Application Data

(60) Provisional application No. 61/769,940, filed on Feb. 27, 2013.

(51) Int. Cl.
*A61B 6/00* (2006.01)
*A61B 10/04* (2006.01)
(Continued)

(52) U.S. Cl.
CPC ............ *A61B 10/04* (2013.01); *A61B 5/0075* (2013.01); *A61B 5/0084* (2013.01);
(Continued)

(58) Field of Classification Search
CPC ............ A61B 10/0041; A61B 10/0275; A61B 10/0283; A61B 10/04; A61B 17/3403;
(Continued)

(56) References Cited

U.S. PATENT DOCUMENTS 5,591,160 A    1/1997    Reynard
5,651,783 A    7/1997    Reynard
(Continued)

FOREIGN PATENT DOCUMENTS

DE    10356315 A1    7/2005
GB    2465088 A    5/2010

OTHER PUBLICATIONS

Penco, S. et al, "Stereotactic vacuum-assisted breast biopsy is not a therapeutic procedure even when all mammographically found calcifications are removed: analysis of 4,086 procedures", AJR 195 (2010) pp. 1255-1260.
(Continued)

*Primary Examiner* — George Manuel (57) ABSTRACT

An interventional device, e.g. a Vacuum Assisted Biopsy (VAB) needle, incorporating optical fibers such that biological tissue in a volume at a side of the interventional device can be substantially completely optically probed by optical spectroscopy. In a VAB embodiment, a plurality of optical fiber pairs connected to respective optical ports, are placed at opposite positions along the suction cavity, and they are
(Continued)

readout subsequently allowing to make a map of the tissue properties along the place where the tissue will be cut by the VAB needle. Based on decision software in an optical console, it can be determined whether the tissue present in the cutting cavity is completely normal tissue or not, prior to actually performing the biopsy on the tissue. In this way a well defined end point for VAB is created. In one embodiment, the optical fibers are arranged in a wall structure of a thin sleeve which fits onto existing VAB needles, thus allowing the VAB needle to be upgraded with an optical probing capability.

13 Claims, 7 Drawing Sheets (51) Int. Cl.
| | | |
|---|---|---|
| | A61B 5/00 | (2006.01) |
| | A61B 10/00 | (2006.01) |
| | A61B 10/02 | (2006.01) |
| | A61B 17/34 | (2006.01) |
| | A61B 17/00 | (2006.01) |
| | A61B 17/32 | (2006.01) |

(52) U.S. Cl.
CPC ........ *A61B 5/6848* (2013.01); *A61B 10/0041* (2013.01); *A61B 10/0275* (2013.01); *A61B 17/3403* (2013.01); A61B 10/0283 (2013.01); A61B 2010/0225 (2013.01); A61B 2010/045 (2013.01); A61B 2017/008 (2013.01); A61B 2017/00057 (2013.01); A61B 2017/00199 (2013.01); A61B 2017/00907 (2013.01); A61B 2017/320064 (2013.01); A61B 2505/05 (2013.01); A61B 2562/0233 (2013.01)

(58) Field of Classification Search
CPC ...... A61B 2010/0225; A61B 2010/045; A61B 2017/00057; A61B 2017/00199; A61B 2017/008; A61B 2017/00907; A61B 2017/320064; A61B 2505/05; A61B 2562/0233; A61B 5/0075; A61B 5/0084; A61B 5/6848

See application file for complete search history.

(56) References Cited

U.S. PATENT DOCUMENTS

| | | | |
|---|---|---|---|
| 6,174,307 | B1 | 1/2001 | Daniel et al. |
| 7,769,426 | B2 | 8/2010 | Hibner et al. |
| 8,046,057 | B2 * | 10/2011 | Clarke .................. A61B 5/0066 600/129 |
| 8,206,315 | B2 | 6/2012 | Mark et al. |
| 2003/0064384 | A1 | 4/2003 | Hung et al. |
| 2005/0203419 | A1 | 9/2005 | Ramanujam et al. |
| 2007/0237739 | A1 | 10/2007 | Doty |
| 2009/0192498 | A1 | 7/2009 | Andrew et al. |
| 2009/0326385 | A1 | 12/2009 | Hendriks et al. |
| 2010/0317964 | A1 | 12/2010 | Hendriks et al. |
| 2011/0009772 | A1 | 1/2011 | Braun et al. |
| 2011/0218445 | A1 | 9/2011 | Braun et al. |
| 2011/0251494 | A1 | 10/2011 | Hendriks et al. |
| 2012/0150042 | A1 | 6/2012 | Sun et al. |
| 2014/0121538 | A1 | 5/2014 | Hendriks et al. |
| 2015/0080761 | A1 | 3/2015 | Burney et al. |

OTHER PUBLICATIONS

Nachabe, R. et al., "Estimation of biological chromophores using diffuse optical spectroscopy: benefit of extending the UV-VIS wavelength range to include 1000 to 1600 nm," Optics Express, vol. 18, 2010, pp. 879-888.

Nachabe, R. et al., "Estimation of lipid and water concentrations of scattering media with diffuse optical spectroscopy from 900 to 1600 nm," Journal of Biomedical Optics, vol. 15, May 2010, pp. 037015-10.

Nachabe, R. et al., "Diagnosis of breast cancer using optical spectroscopy from 500 to 1600 nm: a comparison of classificaiton methods", J. Biomed. Opt. 16 (2011) p087010.

Farrell, T.J. et al, "A diffusion theory model of spatially resolved, steady-state diffuse reflectance for the non-invasive determination of tissue optical properties," Med. Phys. 19 (1992) p. 879-888.

Zhang, Q. et al, "Turbidity-free fluorescence spectroscopy of biological tissue", Opt. Lett. vol. 25 No. 19 (2000) p. 1451-1453.

Torzilli, G. et al. "Contrast-enhanced intraoperative ultrasonography: a valuable and not any more monocentric diagnostic technique performed in different ways", Letters to the Editor, Annals of Surgery, vol. 245, No. 1, Jan. 2007, pp. 152-158.

Hunerbein, M. et al. "Ductoscopy and intraductal vacuum assisted biopsy in women with pathologic nipple discharge", Breast Cancer Res Treat. Oct. 2006, 99(3):301-7.

Hunerbein, M. "Ductoscopic biopsy of papillary tumors in women with nipple discharge", Annals of surgery, 245(1), 2007.

Devicor Medical Products. Mammotome Biopsy System Available from: http://www.mammotome.com/Mammotome/Mammotome-Biopsy-System.

* cited by examiner

OPTICAL GUIDED VACUUM ASSISTED BIOPSY DEVICE

CROSS-REFERENCE TO PRIOR APPLICATIONS

This application is the U.S. National Phase application under 35 U.S.C. §371 of International Application Serial. No. PCT/IB2013/059,387, filed on Oct. 16, 2013, which claims the benefit of U.S. Application Ser. No. 61/769,940, filed on Feb. 27, 2013. These applications are hereby incorporated by reference herein.

FIELD OF THE INVENTION

The present invention relates to the field of medical devices, equipment, interventional devices, and surgical tools. More specifically, the invention relates to a vacuum assisted biopsy device with optical guiding means.

BACKGROUND OF THE INVENTION

In order to diagnose breast cancer, breast biopsies are performed. Various types of breast biopsy exist such as fine needle aspiration (FNA), core needle biopsy (CNB) which can be performed under ultrasound or under X-ray guidance (stereotactic biopsy), vacuum-assisted biopsy (VAB), incisional biopsy (IB) or an excisional biopsy (EB). In a FNA a thin needle is used to harvest a small amount of cells for cytological inspection. In a core needle biopsy typically a 16 or 14 gauge biopsy needle is used to obtain a tissue specimen that allows histological investigation. Typically more than one biopsy is taken per procedure in order to obtain sufficient tissue that allows staging of the tumor (in situ versus invasive). Since more than one biopsy is taken, multiple needle insertions are required. VAB is similar to CNB with the difference that tissue in sucked into the device such that multiple biopsy samples can be harvested with only one needle insertion. The IB and EB are invasive surgical procedures in which a surgeon uses a scalpel to cut through the skin to remove either a piece (IB) or the complete lesion including some margin (EB). This last procedure is in fact a lumpectomy.

In the case of VAB multiple biopsies can be taken. In principal it is possible to remove the complete lesion by continuously removing tissue until no tumor tissue is left. A problem with this is that currently the end point where to stop the VAB is not well defined. Currently VAB is continued until all the calcifications visible under X-ray are removed. Recent investigations have shown however that this is not a reliable way of defining the end point in removing the tumor [S. Penco, S. Rizzo, A. C. Bozzini, A. Latronico, S. Menna, E. Cassano, M. Bellomi, "*Stereotactic vacuum-assisted breast biopsy is not a therapeutic procedure even when all mammographically found calcifications are removed: analysis of 4,086 procedures*", AJR 195 (2010) pp. 1255-1260]. If the VAB had a well defined end point it would have the potential to replace the widely used lumpectomy procedure (open surgery) to remove the tumor with a single needle insertion procedure. This would imply less patient trauma and significantly reducing the cost of the procedure.

In case of tissue ablation, such as isothermal ablation of cancer tumors, a physician inserts the ablation needle to a proper position for treatment, however often an additional device is required, e.g. a scanning device, to guide the physician to the desired position. Further, the physician has no tissue feedback of progress as to how far the ablation zone has reached, and therefore the end point for the procedure is not well defined.

SUMMARY OF THE INVENTION

It would be advantageous to provide an interventional device, e.g. a medical biopsy device, capable of assisting a physician with finding a suitable end point for removing tissue in a vacuum assisted biopsy procedure, or for assisting a physician in positioning of an ablation needle and to provide feedback regarding a progress during a tissue ablation procedure.

In a first aspect, the invention provides an interventional device comprising
  an interventional structure arranged for being inserted into biological tissue, and
  a plurality of optical fibers externally accessible in one end and connected to optical ports in their opposite end, wherein the optical ports are spatially distributed on surface portions of the interventional structure, in order to allow optical probing of biological tissue present in a volume positioned to a side of the interventional structure, upon application of an optical signal to one of the plurality of optical fibers and detection of an optical response thereto at another one of the plurality of optical fibers.

In a sub-aspect, the interventional device comprises a biopsy device,
  wherein an interventional structure of the biopsy device is arranged for being inserted into biological tissue and for taking a biopt thereof, wherein the interventional structure comprises a cavity, e.g. an elongated cavity, into which a part of the biological tissue can be sucked upon application of a negative pressure, wherein the interventional structure comprises a hole through which the biopt can be sucked upon application of a negative pressure, and
  wherein the optical ports are spatially distributed so as to cover different longitudinal positions of the cavity, in order to allow optical probing of biological tissue present in the cavity, upon application of an optical signal to one of the plurality of optical fibers and detection of an optical response thereto at another one of the plurality of optical fibers.

Such interventional device, e.g. in the form of a Vacuum Assisted Biopsy (VAB) device, is advantageous, since it allows optical probing of the biological tissue when sucked in place for cutting in the cavity of the biopsy needle, and thus allows a medical inspection of the piece of tissue before it is cut. Thus, in case of using the biopsy device for removing a tumor, it is possible to test a volume of the biological tissue for the presence of tumor cells prior to cutting the volume of tissue. Therefore, the biopsy device can be used to help a physician in where to end a biopsy procedure. E.g. the device is highly suited within oncology, e.g. for breast cancer.

The plurality of optical ports may be used in pairs, i.e. each comprising an optical source port and optical detector ports positioned with a mutual distance, each pair allowing optical probing of one volume of the biological tissue, i.e. application of optical signals to the optical source ports and detecting the resulting optical output signal at the optical detector ports. Such pairs can then be distributed along a longitudinal extension of the cavity, thus serving to cover the total volume, or at least the majority of volume of biological tissue present in the cavity, when sucked into the cavity and prepared for cutting.

The invention is highly suitable in connection with the working principle of known Vacuum Assisted Biopsy (VAB) device, i.e. where the interventional structure comprises a needle shaped obturator, e.g. of metal, with the cavity formed as a notch in the needle geometry, and where vacuum holes are placed in the cavity to allow a volume of biological tissue to be sucked into the cavity. A cutter serves to cut the tissue present in the cavity, and the resulting biopt can be transported away from the cavity through the hole adjacent to the cavity by means of applying a negative pressure. The negative pressure allows the tissue to be sucked into the cavity and, after having been cut, to be sucked away into a container or the like. This negative pressure is also termed underpressure or vacuum, although in a VAB this vacuum is typically not a true vacuum where all gases are absent.

By 'optical fiber' is understood a suitable light guide arranged for effective transmission of optical energy from one end to the opposite end, such as will be appreciated by the skilled person.

In the following, a number of embodiments will be described.

In one sub-aspect, the interventional structure comprises a sleeve with a wall forming a hollow space, and wherein the plurality of optical fibers are arranged at least partly within a structure of the wall. Such embodiments are advantageous, since the sleeve can be shaped to fit onto an existing interventional instrument, e.g. a biopsy devices, such as a VAB needle, or it can be shaped to fit onto an existing ablation device. Hereby, it is possible to upgrade an existing interventional device with the optical probing properties by means of a rather simple add-on sleeve and associated optical probing console connected thereto. Still, it is possible to provide a thin sleeve with a wall formed in a suitable material and with the optical fibers fully or partly embedded in the wall structure of the sleeve. Thus, the sleeve can be formed such that the presence of the sleeve around the interventional instrument does not disturb the function of the instrument, and such that the thickness of the sleeve is insignificant with respect to a resulting increase in diameter of the interventional part.

Especially, the sleeve may be formed with an opening in the wall structure, thus forming a cavity in the sleeve shaped and positioned to fit a corresponding cavity or notch of an associated VAB needle, and wherein the optical fibers end in optical ports positioned in the wall structure, so as to allow optical probing of biological tissue when present in the cavity. Especially, at least a first optical port may be arranged at a surface part of the wall, so as to direct light outside the sleeve in a direction perpendicular to a longitudinal extension of the sleeve, upon application of an optical signal. Further, at least a second optical port may be arranged at another surface part of the wall, so as to allow receipt of an optical response to said light from biological tissue present in a volume positioned to a side of the sleeve. More specifically, said at least first optical port may be connected to an optical fiber arranged within a structure of the wall following at least a part of a helical pattern, so that a vector along said optical fiber points outside the sleeve at said at least first optical port. In some embodiments of the sleeve, it may be preferred that at least the first optical port is located near the tip of the needle, when the sleeve is placed for normal use e.g. on an associated VAB needle. Further, it may be preferred that at least one optical port is located before the notch of the VAB needle or before the ablation zone in case the sleeve is used on an associated ablation needle. It may be preferred that an optical port is located near the VAB notch and one significantly before the VAB notch. This has the advantage that a comparison measurement can be done between the tissue at the notch and the tissue several cm before the notch. If this distance is tuned well, a measurement in normal tissue and tumor tissue can be compared within one measurement. Still further, it may be preferred that the sleeve around an associated VAB needle comprises a plurality of optical ports positioned such that the tissue suction area of the associated VAB needle is substantially completely probed by optical spectroscopy. Thus, a number of optical port pairs, source and detection ports, are placed at opposite positions along the suction cavity, and they can be readout subsequently allowing to make a map of the tissue properties along the place where the tissue will be cut by the VAB needle. Based on a decision software in an associated optical console, it is possible to determine whether the cutting area is completely normal tissue or not. In this way a well-defined end point for VAB is created.

In embodiments, where the mentioned sleeve embodiments are shaped to fit a medical ablation device, optical probing of a volume positioned to a side of the interventional structure allows a physician to find the position of a tumor to be treated. Further, the physician can monitor the tissue during the ablation procedure to evaluate a result of the ablation treatment without the need for introducing a scanner or other monitoring instrument.

In one embodiment, a plurality of optical ports is positioned along the cavity so as to allow optical probing of a total volume of biological tissue present in the cavity. Especially, a plurality of pairs, each comprising an optical source port and optical detector ports positioned with a mutual distance, are distributed along a longitudinal extension of the cavity. Such embodiment allows performing a plurality of optical probings, i.e. application of optical signals to the optical source ports and detecting the resulting optical output signal at the optical detector ports.

In one embodiment, the interventional structure has a needle geometry, and wherein the optical fibers are arranged in a wall of an obturator of the interventional structure, along an axis of rotation of the needle geometry.

The optical fibers may be arranged within a boundary of the interventional structure, especially the optical fibers may be arranged embedded in an interventional structure.

In one embodiment, each of the plurality of optical fibers is connected to one single optical port. Thus, in such embodiment, one optical fiber can emit or receive a light signal from one spatially well-defined position in the cavity, since it is preferred that the optical port opening areas are small compared to a surface area of the cavity.

It is to be understood that the number of optical ports is preferably selected to match the geometry of the cavity or volume to be probed, such that it is possible to optically probe the total volume of, or at least the majority of volume of, the biological tissue in the cavity or total volume to be covered. Thus, the number of optical ports may be two, however preferably 4-8, or 8-12, or more.

Pairs of optical source ports and optical detector ports may be positioned with one common distance. Especially, a pair of an optical source port and an optical detector port may be positioned on a line perpendicular to a longitudinal axis of the interventional structure, and subsequent pairs of optical source ports and optical detector ports are then positioned with one common distance. Thus, preferably covering the entire length of the cavity by evenly distributed optical ports.

The optical ports may be formed as respective openings in a wall of an obturator of the interventional structure. Especially, the optical ports may be formed as circular holes. The optical ports may be formed as openings sealed by one of: an optically transparent resin, an optically scattering resin. Such resin prevents biological tissue from penetrating into the port opening, and preferably the resin surface is formed to be flush with a surface of the cavity.

In one embodiment, a plurality of optical ports are arranged on a first straight line parallel with a longitudinal axis of the interventional structure, and wherein a plurality of optical ports are arranged on a second straight line parallel with the first line. Especially, the optical ports on the first straight line can be used as optical source ports, and the optical ports on the second straight line can be used as optical detector ports. This allows optical probing of the biological tissue at a plurality of positions along the cavity.

Subsequent pairs of optical source ports and optical detector ports may be positioned with a distance being smaller than a distance between optical source ports and optical detector ports. This allows overlapping optical probing of the biological tissue along a longitudinal axis of the cavity. Especially, subsequent pairs of optical source and detector ports are arranged at a distance allowing optical probing of overlapping volumes of the biological tissue.

The cavity of the interventional structure may have a plane bottom portion, and wherein the plurality of optical ports is spatially distributed on this plane bottom portion. A plurality of holes may be provided on this plane bottom surface and being arranged for connection with an external vacuum suction system allowing the biological tissue to be sucked into the cavity.

In one embodiment, optical fibers connected to pairs of optical source ports and optical detector ports are arranged in respective planes which are parallel to the plane bottom portion of the cavity.

In one embodiment, the optical ports are geometrically distributed such that one optical source port forms a pair with two or more optical detector ports. In the same manner, the optical ports are geometrically distributed such that one optical detector port may form a pair with two or more optical source ports.

Preferably, the interventional device comprises a console with at least one light source and a light detector, wherein the console is arranged for connection to the optical fibers, e.g. via an optical connector, so as to allow emission of an optical signal from the light source to a first selection of the optical ports, and to allow receipt of light from a second selection of the optical ports. In one embodiment, the console comprises a processor capable of determining respective measures of spectral contents of optical signals received from the second selection of the optical ports, and wherein the console is arranged to generate an output indicative of respective states of the biological tissue present at different longitudinal positions in the cavity or volume to be probed. Especially, the console may be arranged to generate an output indicative of the presence of tumor cells in the biological tissue. In some embodiments, the console may be arranged to emit an optical signal being one of: a diffuse reflectance spectroscopy signal, a fluorescence spectroscopy signal, a Raman spectroscopy signal, a diffuse optical tomography signal, an optical coherence tomography signal, and a differential path length spectroscopy signal.

Embodiments where the interventional device comprises a biopsy device, may comprise an optical probe head arranged for optical scanning of a biopt after being taken by the interventional structure and transported away there from through the hole. Such embodiment allows the biological tissue to be optically probed both before being cut, i.e. when present in the cavity, and again after being cut, e.g. during transport in a transparent hose. This increases the reliability of the testing of the biological tissue, e.g. increasing the chance of detecting tumor cells if present in the biopt.

It is to be understood that the system according to the first aspect can be used in a number of applications, such as detecting and/or removing tumor tissue, ensuring that a target tissue is actually present at the biopsy device before taking the biopsy. Apart from medical applications, the biopsy device can be used e.g. for testing of food, such as meat or other biological material.

In a second aspect, the invention provides a method for determining a state of a biological tissue, the method comprising providing light to a first position of the biological tissue when present in a volume positioned at a side of an interventional structure of an interventional device, detecting an optical response from the biological tissue at a second position, calculating a measure of a state of the biological tissue according to the detected optical response, and generating an output indicative of the state of the biological tissue.

It is appreciated that the same advantages and embodiments of the first aspect apply as well for the second aspect. In general the first and second aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

In the prior art, Vacuum Assisted Biopsy (VAB) needle or cannula are known, e.g. available from Devicor Medical Products, e.g. for performing biopsy in treating and diagnosing breast cancer. In such devices small sucking holes are embedded at the bottom of a notch forming a cavity in the interventional structure, which allow for sucking tissue into the cavity for facilitating the tissue cutting. A larger sucking hole adjacent to the cavity is then used for removing the cut tissue volume from the notch. In a normal procedure, the needle is positioned under the lesion. The tissue is then sucked (vacuumed) into the cavity, the tissue is cut by means of a cutter, and after completion of the cutting, the biopt is sucked away from the cavity via the hole adjacent to the cavity, and transported away from the interventional structure. The tissue is sucked into the cavity by applying a negative pressure (underpressure). After having been cut, the tissue is sucked out of the cavity and transported away, again by application of a negative pressure. The amount of negative pressure for transporting the tissue (the transportation negative pressure) need not be the same as the amount of negative pressure for sucking the tissue into the cavity (the sucking negative pressure).

Figures 1A, 1B:
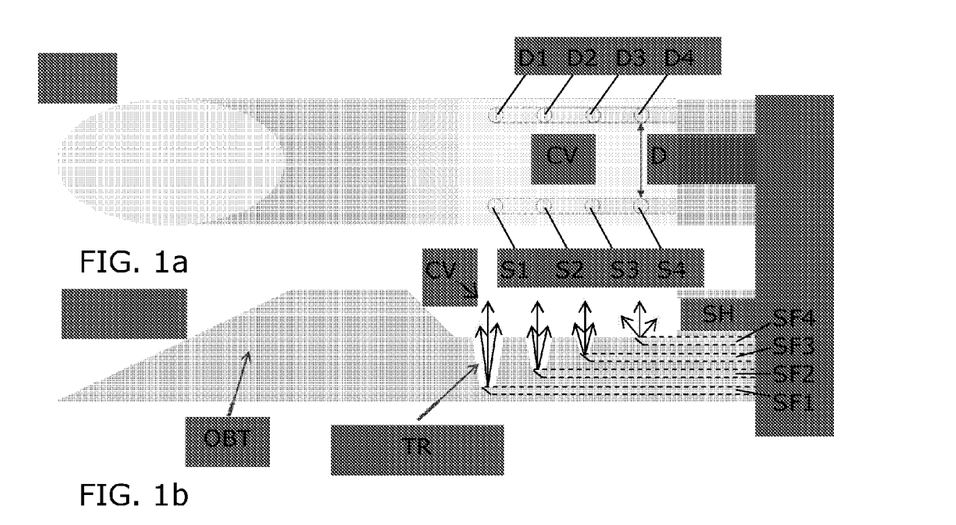
FIGS. 1a and 1b illustrate sketches of one biopsy device embodiment with one configuration of optical ports.

FIGS. 1a and 1b illustrates a top view and a side view, respectively, of an interventional structure embodiment according to the invention which is needle shaped. Optical fibers SF1, SF2, SF3, SF4, i.e. light guides, are integrated in a wall of the obturator OBT along a axis of rotation of the needle structure, with the optical fibers SF1, SF2, SF3, SF4 extending up to the cavity CV area, where the cavity CV is formed as a notch with a plane bottom part. Optical fibers SF1, SF2, SF3, SF4 are externally accessible in one end and in their opposite end, they are optically connected to respective optical ports S1, S2, S3, S4 formed as opening in the obturator OBT and arranged at the plane bottom part of the cavity CV. On one side of the plane bottom part, four optical source ports S1, S2, S3, S4 are positioned on a straight line, and on the other side of the plane bottom part, four optical detector ports D1, D2, D3, D4 are positioned on another straight line. Both lines are parallel with a longitudinal axis of the needle structure. The optical detector ports D1, D2, D3, D4 are connected to respective optical fibers.

For a consistent characterization of the entire cavity area with an array of multiple source-detector fiber pairs, it is preferred to ensure that, for each optical fiber pair (S1, D1), (S2, D2), (S3, D3), (S4, D4), the source-detector distances D are the same.

This can be achieved by guiding parallel bundles of optical fibers SF1, SF2, SF3, SF4 to the cavity area CV, whereby the plane of the tip of the fibers SF1, SF2, SF3, SF4 have an inclination of 45° relative to the axis of rotation to allow for redirecting the light into the cavity CV volume. Both optical source and detector fibers are aligned parallel to the axis of rotation of the needle.

The light from the optical source fibers SF1, SF2, SF3, SF4 is coupled out through optical ports formed as holes S1, S2, S3, S4 in the obturator structure OBT in the cavity area CV in a direction perpendicular to the axis of rotation of the needle. The holes S1, S2, S3, S4 can be sealed by a transparent, non-scattering resin TR that prevents the holes S1, S2, S3, S4 from being filled up by fluids or tissue fragments. A parallel set of optical detector fibers are positioned on the opposite side of the cavity CV with a defined source-detector fiber tip distance D. This ensures that the optical spectra collected from each source-detector fiber pair probes a biological tissue volume of comparable dimensions, and that each probed volume can be analyzed by an optical console in a consistent way. This allow for a complete quantitative mapping of the biological tissue present in the cavity area CV.

In this embodiment, the parallel optical fiber bundles are in a plane perpendicular to the plane of the plane bottom part of the cavity CV. This optical fiber arrangement would allow to combine the optical tissue characterization with mechanism for sucking tissue into the cavity similar to prior art system as described above, and also for sucking tissue away from the cavity CV through the hole SH.

Figure 2:
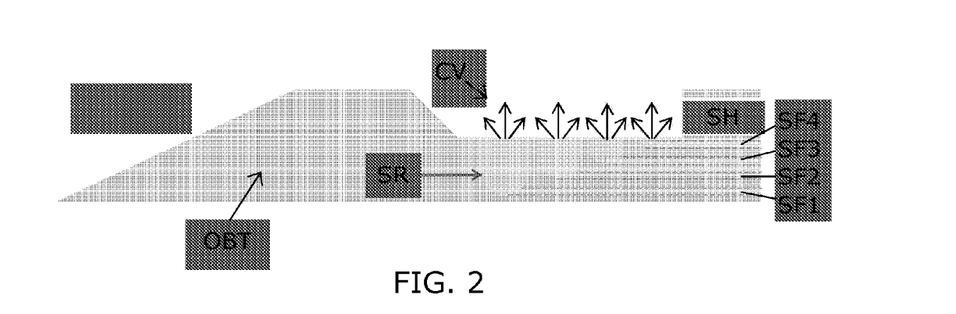
FIG. 2 illustrates a sketch of another embodiment with an alternative configuration of optical ports.

FIG. 2 shows another embodiment similar to the needle structure of FIGS. 1a and 1b, but differing with respect to the way the optical fibers SF1, SF2, SF3, SF4 are coupled to respective optical ports. In this embodiment, highly scattering, but non-absorbing resin SR is used to guide the light from the stacked optical fibers SF1, SF2, SF3, SF4 towards the cavity area CV. The composition of the resin SR and the dimensions of the individual holes containing the resin SR should be chosen in a way to maximize the light gain for each optical fiber SF1, SF2, SF3, SF4. For instance, choosing larger openings for the optical fibers which are further away from the cavity area CV can ensure that each optical source-detector fiber pair collects a comparable amount of scattered light, regardless of its location relative to the cavity CV.

Figure 3A:
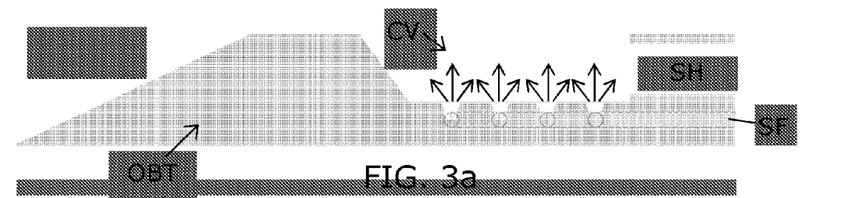
FIGS. 3a, 3b, 3c illustrates sketches of different examples of geometries of optical ports and arrangements of optical fibers in one plane.
Figure 3B:
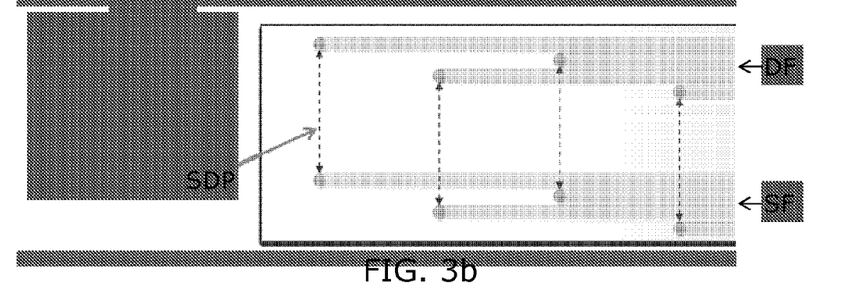
Figure 3C:
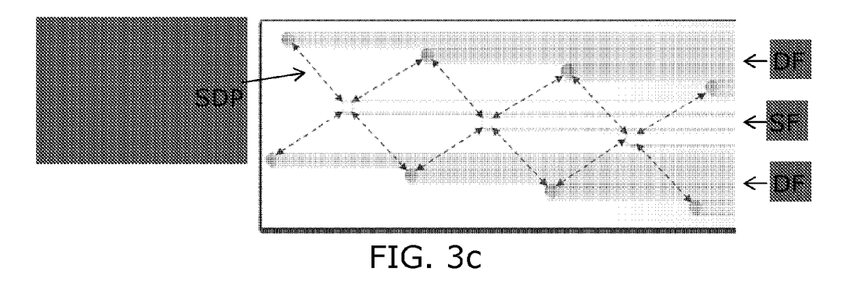

FIGS. 3a, 3b, and 3c show other embodiments, still for a structure similar to the needle structure of FIGS. 1 and 2, but differing with respect to the arrangement of the optical fibers SF, DF and optical ports forming source-detector pairs SDP. In these embodiments, the optical fibers SF, DF are arranged in a plane parallel to the plane bottom of the cavity CV. This ensures that all optical fiber ends have the same distance from the plane of the cavity CV to facilitate a uniform tissue characterization.

Optical fiber bundles can be arranged parallel to each other in a plane in a non-overlapping way. FIG. 3a shows the needle structure with obturator OBT and cavity CV seen from the side. In FIGS. 3b and 3c, examples are given for optical fiber arrangements that allow for a comprehensive characterization of the biological tissue present in the cavity CV area. In FIG. 3a, source-detector pairs SDP are arranged on lines perpendicular to the longitudinal axis of the needle, whereas in FIG. 3b, one optical source port forms a source-detector pair SDP with four optical detector ports, thus providing source-detector pairs SDP with an angle, here approximately 45°, with the longitudinal axis of the needle.

Figures 4A, 4B, 4C:
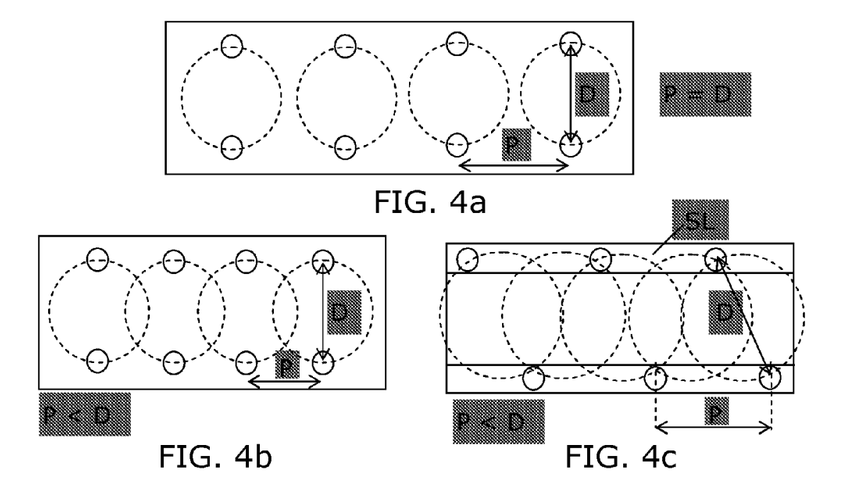
FIGS. 4a, 4b and 4c illustrate different examples of geometries of pairs of optical source and detector ports.

FIGS. 4a and 4b illustrate two examples of configurations of optical source and detector pairs of optical ports indicated as circular holes, which are each capable of optically probing a volume of biological tissue, here indicated with dashed lines. In FIG. 4a, the distance P between subsequent optical fiber pairs is equal to the distance D of the optical source and detector ports of each pair, resulting here in non-overlapping volumes, i.e. leaving volumes of the tissue which is not probed. In preferred embodiment, as in FIG. 4b, the distance P between subsequent optical fiber pairs is smaller than the distance D of the optical source and detector ports of each pair. Generally, the volume probing depth is characterized by a length which corresponds to one half of the distance between the source and the detector fiber end points. Thus, for a complete characterization of the tissue volume in the notch, the parameter P should at least equal the parameter D, i.e. P≤D. For P<D, the tissue volumes probed by each optical source-detector pair would partially overlap, which can add more confidence in the assessment of the acquired spectra. Preferably, in case P=0.5*D, each volume section of the tissue in the cavity is probed twice by two different source-detector fiber pairs, which can increase the sensitivity and make the data analysis more robust, and thereby improve the quality of the feedback to the physician.

FIG. 4c shows yet another configuration example of source-detector pairs illustrated in a manner similar to FIGS. 4a and 4b. In this example, the optical ports on each side are longitudinally displaced by 0.5*P, and thus probing of 5 different volumes is possible with only 6 optical ports (and 6 optical fibers associated therewith). In this case, the relation between the distances D, P is: D<P≤√2*D. In this configuration example, the locations of the optical ports are indicated as positioned in an edge wall of a sleeve SL to be fitted around a VAB needle.

It is to be understood that in principle the different configurations shown in FIGS. 4a, 4b, and 4c can all be applied to embodiments where optical fibers are incorporated in a biopsy device, e.g. a VAB needle, as well as to embodiments where the optical fibers are incorporated in a sleeve.

Figure 5:
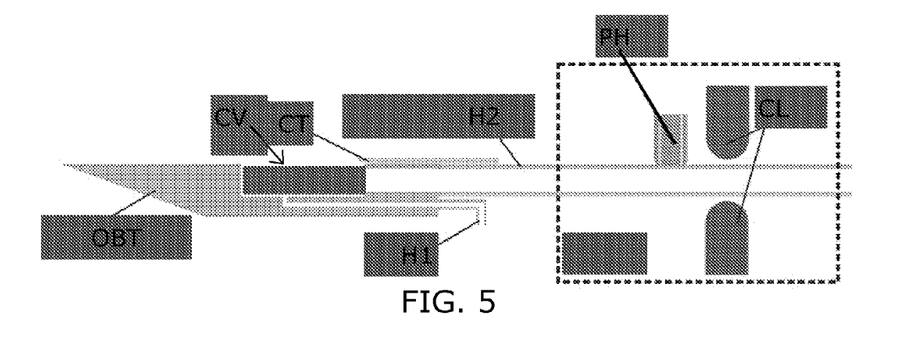
FIG. 5 illustrates an embodiment with an optical probe head for probing a biopt after being transported away from the interventional structure.

FIG. 5 shows an embodiment, e.g. one of the previously described VAB needles, where a cavity CV formed in an obturator OBT of a biopsy needle with a hose H1 arranged for applying a negative pressure (vacuum) to suck the biological tissue into the cavity CV via one or more small holes in the bottom of the cavity. The optical fibers and ports are not shown here, for simplicity. A cutter CT is arranged for being moved forward for cutting the biological tissue present in the cavity. A resulting biopt can then be sucked out of the cavity CV and into a transparent hose H2 and into an area of the hose H2 where an optical probing head PH and switchable obstruction clamps CL are placed, and capable of providing an optical scanning of the biopt, i.e. in addition to the optical probing already performed on the tissue while present in the cavity CV, before being cut. In this way an additional investigation of the tissue sample on the presence of tumor tissue can be performed which increases the robustness of the tissue discrimination.

The workflow of the embodiment of FIG. 5 may be as follows: a) The biopt is taken. b) The clamps CL clamp together and create an obstruction by narrowing the diameter of the hose H2. When the biopt is sucked into hose H2, it is stopped by the obstruction. c) The photonic tools probe head PH scans over the biopt. From the spectra, one determines whether the biopt contains tumor tissue or not and where along the length of the biopt the timorous tissue is located. This information is presented to the physician. d) When the scanning is finished, the clamps CL part and the biopt is sucked out to be delivered to histopathology. Preferably, the results of the second measurement after the resection of the tissue are correlated with the first measurement at the suction opening of needle. Only when both measurements indicate no tumor present a signal, for instance a green light is produced. When one of them indicates tumor while the other does not, an orange light is given and when both indicate tumor a red light is produced. In this way the detection system becomes more robust.

Figure 6:
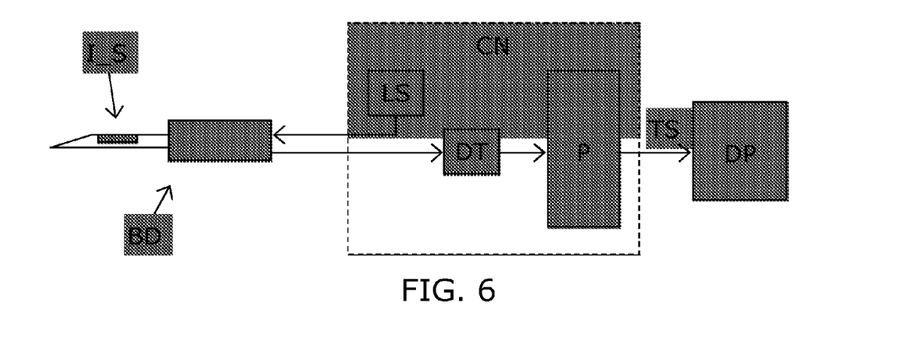
FIG. 6 illustrates a block diagram of an embodiment with a console capable of determining a tissue state of the biological tissue being probed when present in the cavity of the interventional structure.

FIG. 6 illustrates a block diagram of an embodiment where the biopsy device BD comprises an interventional structure I_S in the form of a needle geometry or cannula, e.g. as one of the embodiment described above. Via a handle, the optical fibers of the interventional structure I_S are connected to an optical console CN comprising at least one light source LS for generating an optical signal to be applied to source optical fibers, and an optical detector DT serving to receive response optical signals from detector optical fibers. In a specific embodiment, the light source LS is a form of a halogen broadband light source with an embedded shutter. The optical detector DT can preferably resolve light with a wavelength substantially in the visible and infrared regions of the wavelength spectrum, such as from 400 nm to 1700 nm. The optical ports of the interventional structure I_S allow for measurements of Diffuse Reflectance Spectrum (DRS). For details regarding DRS, see [R. Nachabé, B. H. W. Hendriks, M. V. D. Voort, A. E, and H. J. C. M. Sterenborg, "Estimation of biological chromophores using diffuse optical spectroscopy: benefit of extending the UV-VIS wavelength range to include 1000 to 1600 nm," Optics Express, vol. 18, 2010, pp. 879-888] and [R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm," *Journal of Biomedical Optics*, vol. 15, May. 2010, pp. 037015-10].

The console comprises a processor P which receives signals from the optical detector DT, and preferably the processor is programmed to calculate for each source-detector pair of optical fibers, a measured DRS. The processor P preferably transforms the measured spectra into physiological parameters that are indicative for the tissue state for each source-detector pair. The information is then checked if there are signatures of tumor tissue present. If so, then the procedures of removing tissue will be continued, if not a signal will be produced that in this location a tumor is detected. Hence prior before a new biopsy is taken a set of DRS are collected for each source detector pair. Each measured DRS is analyzed, and results in a signal whether tumor tissue is still present or not, i.e. an output indicative of the tissue state TS, which may be presented via a display DP. When all the DRS results is tumor free, the tissue in contact with the needle is tumor free and a signal will be produced to indicate this to the physician.

To determine whether tumor tissue is present the signal for each source-detector pair can be compared with a look-up-table. Another way is to translate the measured parameters into physiological parameters and define ranges for these parameters where the tissue is normal compared to tumor. See e.g. [R. Nachabé, D. Evers, B H W Hendriks, G W Lucassen, M. Van der Voort, E J Rutgers, M-J Vrancken Peeters, J A van der Hage, H S Olderburg, J. Wesseling and T J M Ruers, "Diagnosis of breast cancer using optical spectroscopy from 500 to 1600 nm: a comparison of classification methods, J. Biomed. Opt. 16 (2011) p087010] where methods based on classification and regression tree (CART) methods are described for classifying tissue in tumor and normal based on these physiological parameters. In the following, further details regarding an algorithm for extracting various physical parameters will be described.

In a more specific embodiment the console CN is capable of importing an image made by an imaging modality like X-ray, CT, MRI, US, PET-CT. Preferably, in these images the needle tip of the interventional structure I_S is visible such that the information obtained by spectroscopy can be correlated with the image information. In this way the image can provide the coarse guidance for the tumor removal with the vacuum assisted biopsy device BD while the optical information provides the fine guidance. Since most of these biopsies are performed stereotactically this imaging information will be available.

The information regarding the progress and whether the area in contact with the interventional device still contains tumor tissue can be provided in several ways to the physician using the D. A target indicator can be applied to the display, e.g. a highlighting in the form of a color, a shading, or the like. A light indicator can additionally or alternatively be used, e.g. showing with red light if still tumor tissue is detected, and with green light indicating that no tumor and/or optional with yellow, the system suspects tumor. Another way is using a sound signal. In yet another way, a probability of tumor detection as a bar can be shown on the display DP.

Although DRS is described above to extract tissue properties, it is understood that other optical methods can be envisioned like diffuse optical tomography by employing a plurality of optical fibers, differential path length spectroscopy, fluorescence and Raman spectroscopy.

Figure 7A:
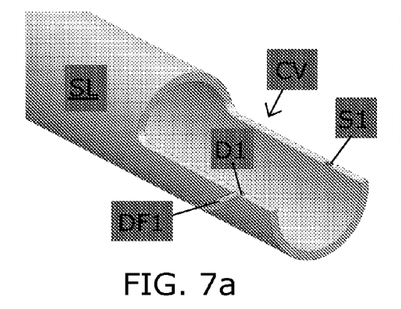
FIGS. 7a and 7b illustrate two views of a sleeve embodiment suited to fit onto a VAB needle with optical fibers partly embedded in the sleeve wall.
Figure 7B:
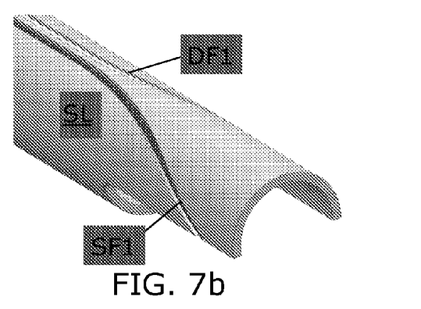

FIGS. 7a and 7b illustrate two different 3D views of an interventional device in the form of an optical sleeve SL suited to fit onto an associated VAB needle (not shown), thus adding optical probing capability to an existing VAB device. The sleeve SL is formed as a thin wall forming a hollow tube with a circular cross section. In a proximal end (not visible), the sleeve SL has an opening to allow an associated VAB needle to enter the hollow part of the sleeve SL. The wall material may be slightly elastic, so as to ensure that the wall structure of the sleeve SL fits tightly around the VAB needle, when the sleeve SL is mounted on the VAB needle. The distal end of the sleeve SL is also open to allow the tip of the VAB needle to protrude in front of the distal end of the sleeve SL. Further, the towards the distal end, the sleeve SL has an opening in the form of a cut away in a side of its wall structure, thus forming a cavity CV. When positioned for use on an associated VAB needle, the cavity CV of the sleeve SL preferably coincides with a corresponding cavity or notch of the VAB needle.

In the illustrated embodiment two optical fibers SF1, DF1 are integrated in the wall structure of the sleeve SL by being positioned in grooves in the wall structure of the sleeve SL. The optical fiber SF1, DF1 ends form respective optical ports S1, D1 positioned on each side of the cavity CV, so as to allow one optical port S1 to function as optical source port for applying light, and to allow the other optical port D1 on the opposite side of the cavity CV to receive a light response from biological tissue positioned in a volume to the side of the sleeve SL, i.e. a volume in and around the cavity CV, thus also in the cavity or notch of an associated VAB needle, when mounted thereon for normal use.

In FIGS. 7a and 7b, the optical fibers SF1, DF1 are integrated in the wall of the sleeve SL in a helical way such that a vector along the optical fibers SF1, DF1 at the fiber ends, i.e. at the optical ports S1, D1, point outside the sleeve SL. In this way the probing volume can be tuned such that a significant volume of the tissue is probed perpendicular to the needle. In the shown example, the optical fibers SF1, DF1 end at respective wall edges of the opening forming the cavity CV in the sleeve SL, thus allowing optical probing of a biological tissue positioned in and around the cavity CV.

Figure 8A:
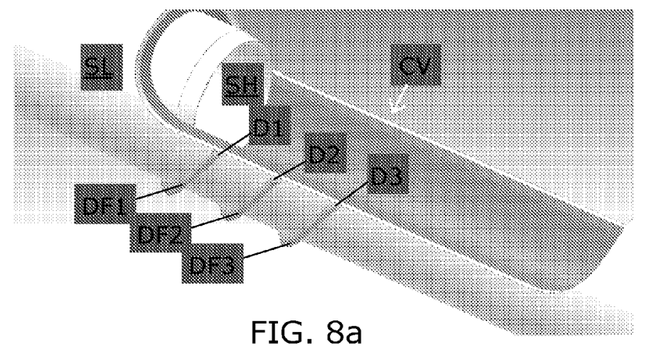
FIGS. 8a and 8b illustrate two views of a sleeve embodiment placed on a VAB needle.
Figure 8B:
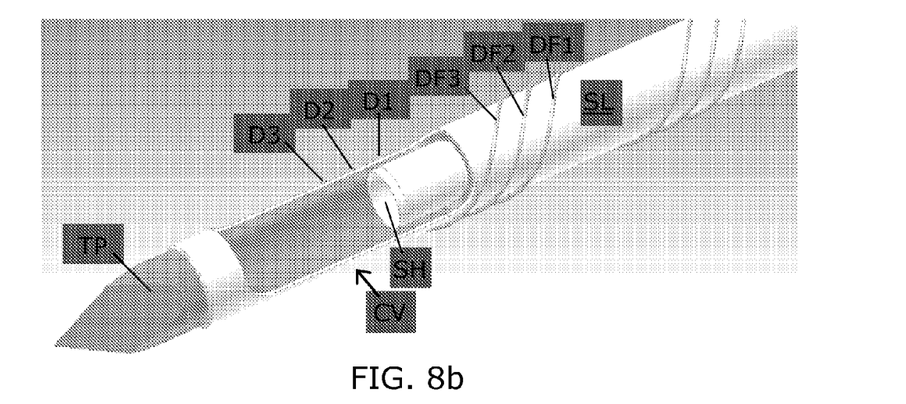

FIGS. 8a and 8b show two 3D views of another sleeve SL embodiment mounted on an associated VAB needle, one of which the tip TP of the VAB needle is visible. In this embodiment, the sleeve SL has a partial cut away in its wall, so as to form an opening which substantially coincides with the cavity CV of the VAB needle. Thus, in this embodiment the sleeve SL also has a hollow portion in front of the cavity CV, namely the distal portion of the sleeve SL towards the tip TP end of the VAB needle.

In this embodiment, three parallel optical fibers are shown DF1, DF2, DF3 arranged in a helical way on a surface part of the wall forming the sleeve SL ending at respective optical ports D1, D2, D3 at respective longitudinal positions along an edge of the wall in the open part of the sleeve SL, i.e. on an edge of the cavity CV of the VAB needle. A suction hole SH for removal of tissue in the cavity CV after being cut is shown in a proximal end of the cavity CV.

It is to be understood that preferably one or more optical fibers and ports (not shown) may be positioned on an opposite edge of the cavity CV to allow optical probing across the cavity CV. Preferably, at least one optical port is located near the VAB notch or cavity CV, and at least one optical port located significantly before the VAB notch or cavity CV. This has the advantage that a comparison measurement can be done between biological tissue at the cavity CV, and biological tissue several cm before the cavity CV. If this distance is tuned well, a measurement in normal and tumor tissue can be compared within one measurement.

Figure 9:
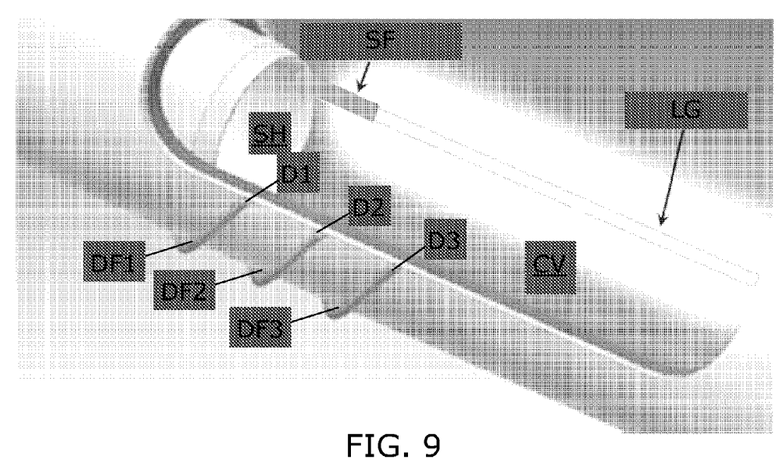
FIG. 9 illustrates a sleeve embodiment for a VAB needle, where light for probing biological tissue in the cavity of the VAB needle is formed by a light guide.

FIG. 9 shows a 3D view of a variant of the embodiment of FIGS. 8a and 8b, namely where a light guide LG is attached to a side wall. A single source fiber SF is attached to this light guide LG arranged to illuminate biological tissue along a side wall of the cavity CV. The length of the light guide LG may especially be equal to the entire longitudinal length of the notch or cavity CV. The detection fibers DF1, DF2, DF3 connected to the optical ports D1, D2, D3 can be positioned and fixed such as explained for the embodiment of FIGS. 8a and 8b. Such assembly has the advantage of minimizing the number of optical source fibers SF to one, in addition to enabling comparative measurements at longitudinal positions with use of optical detector ports D1, D2, D3 positioned at different longitudinal positions along the light guide LG, but opposite the cavity CV. Preferably, the source fiber SF for optically connecting the light guide LG, may be arranged within the VAB needle, or it may be arranged in or on the wall of the sleeve SL in a manner as already described for the other optical fibers SF1, DF1, DF2, DF3 of the sleeve embodiments.

Figure 10:
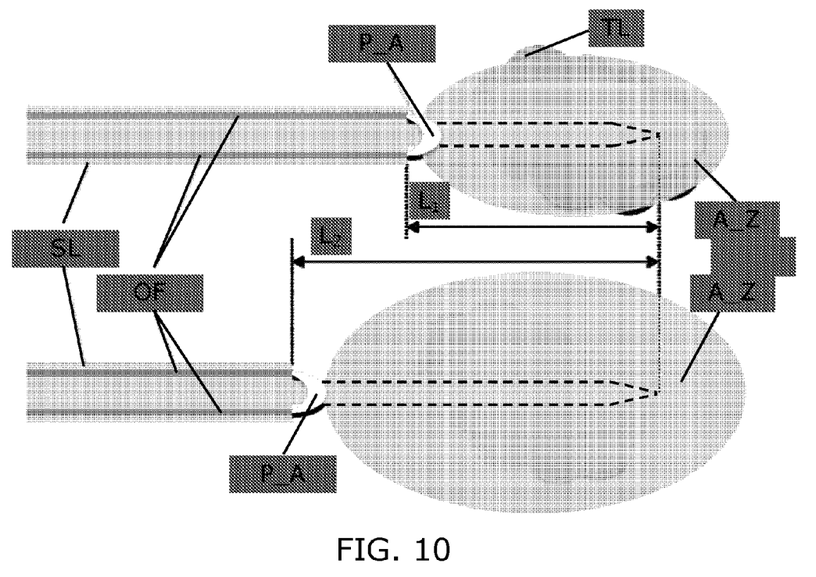
FIG. 10 illustrates two sketches of the principle of a sleeve embodiment fitted onto an ablation device.

FIG. 10 shows two sketches of an optical sleeve SL embodiment mounted around a conventional ablation needle. The integrated optical fibers OF are connected to optical ports towards a distal end of the sleeve SL that allow optical probing of a volume P_V to a side of the ablation needle. This can give tissue feedback to provide decision support for a physician operating the ablation needle in several ways. In case the sleeve SL extends up to the tip of the ablation needle, the tissue feedback allows for an assessment of the correct needle placement in the target region to start the ablation treatment, e.g. Radio Frequency treatment. This is particularly useful for lesions, e.g. tumor lesions TL, where conventional imaging modalities do not allow for proper lesion localization.

In another application, the sleeve SL can also be positioned at a certain fixed distance $L_1$ from the ablation needle tip. The parameter $L_1$ can be chosen by the physician as an indicator for the volume which is about to be treated. For instance, if a tumor lesion TL (including its boundaries) spans a volume with a characteristic distance (radius) from the center of the lesion, as determined e.g. by a CT or MRI scan, then the optical tissue feedback can give information about the progress of the treatment. For instance, the signal from the optically probed volume P_V can indicate changes in tissue parameters during the ablation procedure. The probed volume P_V can be adjusted by choosing the source-detector fiber distance in such a way that only the outer boundary of the targeted ablation region is probed. Then, the optical signal can give an accurate feedback on when the ablation treatment has reached the outer boundary of the target region. This gives the physician a decision point for stopping the procedure and for avoiding over treatment or also under treatment, i.e. the ablation zone did not reach the intended size due to for instance cooling by blood vessels.

Combining the two applications mentioned above, the sleeve can also be designed in a way which allows for re-positioning, or retracting, the sleeve SL during a procedure. For instance, when a procedure is started by inserting the needle, the sleeve SL may cover the needle up to the needle tip, or at a distance $L_1$ away from the needle tip. The optical fibers OF therefore probe the tissue volume P_V in front of the tip and allow for fine-guidance of the needle towards the lesion. Once the lesion is located, the needle remains in its position, whereas the sleeve SL is retracted for a length $L=L_2-L_1$, which corresponds to the desired outer boundary of the planned ablation. The sleeve SL position is then externally fixed at this length $L_2$ away from the needle tip, and the ablation procedure can start. The progress of the treatment is then monitored as described above.

In preferred embodiments for ablation applications, stain resistant optical fibers are used, i.e. optical fibers coated such that no biological compounds adhered to the optical fibers due to RF ablation of the tissue.

Figure 11:
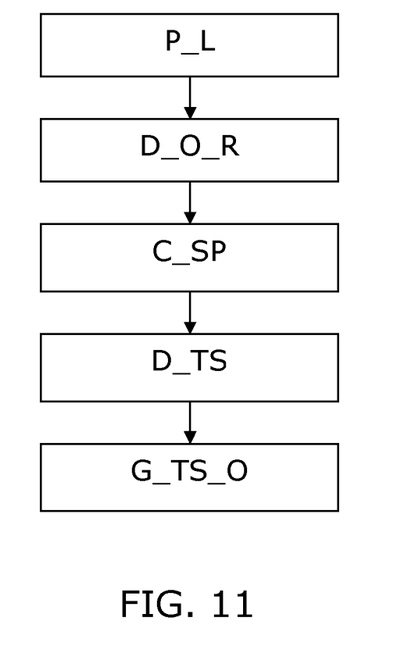
FIG. 11 illustrates a block diagram of steps in a method embodiment.

FIG. 11 illustrates a method embodiment according to the invention for determining a state of a biological tissue, e.g. identifying possible tumor tissue within a human or animal tissue. The method comprises providing a light signal P_to a first plurality of positions of the biological tissue when present in a cavity of a vacuum assisted biopsy device, e.g. a biopsy device according to the first aspect of the invention. Next, an optical response is detected D_O_R from the biological tissue under test. Subsequently, a spectral response C_SP is calculated in accordance with the detected optical response. This spectral response is then used in a step of determining a tissue state D_TS, e.g. determining if there are tumor cells within the biological tissue under test, and finally an output is generated G_TS_O indicative of the determined tissue state. The output may be in the form of a graphical output on a display device, and/or an audible signal according to the determined tissue state. E.g. a calculated optical spectrum may be graphically presented to the operator on a display device. According to the output, a physician or other operator can decide how to proceed the biopsy, especially the output may assist the operator in deciding when to end the biopsy procedure. It is to be understood that some of the steps may be performed in a different order than shown in FIG. 11, and other than in the description of the above method embodiment.

In the following, examples are given regarding details of extraction of features or parameters from one or more optical probe measurements and determining, based thereon, a measure indicative of a state of the biological tissue. An example of extracting a physiological parameter is by fitting the acquired spectra using a custom made Matlab 7.9.0 (Mathworks, Natick, Mass.) algorithm. In this algorithm, a widely accepted analytical model was implemented, namely the model introduced by the reference [T. J. Farrel, M. S. Patterson and B. C. Wilson, "A diffusion theory model of spatially resolved, steady-state diffuse reflectance for the non-invasive determination of tissue optical properties," Med. Phys. 19 (1992) p. 879-888], which is hereby incorporated by reference in entirety. The input arguments for the model of the reference [T. J. Farrel, M. S. Patterson and B. C. Wilson, "A diffusion theory model of spatially resolved, steady-state diffuse reflectance for the non-invasive determination of tissue optical properties," Med. Phys. 19 (1992) p. 879-888] are the 2012PF01543 absorption coefficient $\mu_a(\lambda)$, the reduced scattering coefficient $\mu'_s(\lambda)$ and the center-to-center distance between the emitting and collecting optical fibers. For a complete description of the diffusion theory model, we refer to [T. J. Farrel, M. S. Patterson and B. C. Wilson, "A diffusion theory model of spatially resolved, steady-state diffuse reflectance for the non-invasive determination of tissue optical properties," Med. Phys. 19 (1992) p. 879-888]. The used formulas are mainly based on work of Nachabé et al., and reference is thus made to [R. Nachabé, B. H. W. Hendriks, M. V. D. Voort, A. E, and H. J. C. M. Sterenborg, "Estimation of biological chromophores using diffuse optical spectroscopy: benefit of extending the UV-VIS wavelength range to include 1000 to 1600 nm," Optics Express, vol. 18, 2010, pp. 879-888] which is hereby incorporated by reference in entirety, and furthermore reference is made to [R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm," Journal of Biomedical Optics, vol. 15, May. 2010, pp. 037015-10] which is hereby incorporated by reference in entirety.

A double power law function can be used to describe the wavelength dependence of the reduced scattering, where the wavelength $\lambda$ is expressed in nm and is normalized to a wavelength value of $\lambda_0=800$ nm. The parameter $\alpha$ corresponds to the reduced scattering amplitude at this specific wavelength.

$$\mu_s^*(\lambda) = a\left(\rho_{MR}\left(\frac{\lambda}{\lambda_0}\right)^{-b} + (1-\rho_{MR})\left(\frac{\lambda}{\lambda_0}\right)^{-4}\right) [cm^{-1}] \quad (Eq. 1)$$

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted b and is related to the particle size.

Figure 12:
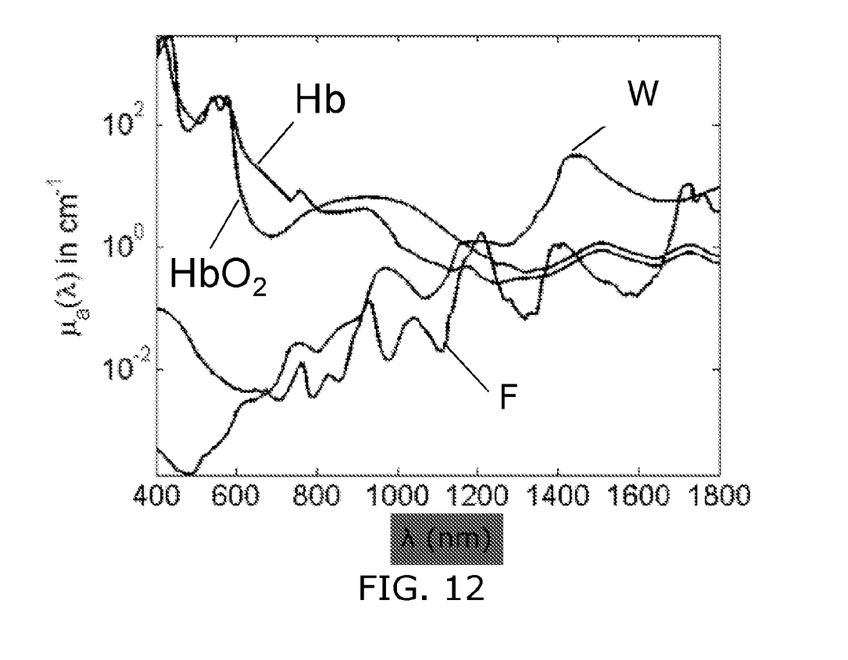
FIG. 12 illustrates a graph showing absorption spectra for blood, water and fat.

FIG. 12 shows logarithmic plots of absorption spectra for blot Hb, Hb0$_2$, water W, and fat F. For a homogeneous distribution of absorbers, the total light absorption coefficient $\mu_a(\lambda)$ can be computed as products of the extinction coefficients and volume fraction of the absorbers shown in FIG. 12:

$$\mu_a^{Total} = f_1\mu_a^1 + f_2\mu_a^2 + f_3\mu_a^3 + \quad (Eq.2)$$

Instead of modeling the absorption coefficient $\mu_a(\lambda)$ as the sum of absorption coefficients weighted by the respective concentrations of the four chromophores of interest, it was decided to express the tissue absorption coefficient as:

$$\mu_a^{Tissue}(\lambda) = C(\lambda)\nu_{Blood}\mu_a^{Blood}(\lambda) + \nu_{WL}\mu_a^{WL}(\lambda)[cm^{-1}] \quad (Eq.3)$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $\nu_{WL}=[Lipid]+[H_2O]$, whereas $\nu_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as:

$$C(\lambda) = \frac{1-\exp(-2R\mu_a^{Blood}(\lambda))}{2R\mu_a^{Blood}(\lambda)} \quad \text{(Eq. 4)}$$

where R denotes the average vessel radius expressed in cm. The absorption coefficient related to blood is given by:

$$\mu_a^{Blood}(\lambda) = \alpha_{BL}\mu_a^{HbO2}(\lambda) + (1-\alpha_{BL})\mu_a^{Hb}(\lambda)[\text{cm}^{-1}] \quad \text{(Eq.5)}$$

where $\mu_a^{HbO2}(\lambda)$ and $\mu_a^{Hb}(\lambda)$ represent the basic extinction coefficient spectra of oxygenated hemoglobin $HbO_2$ and deoxygenated hemoglobin Hb, respectively. The oxygenated hemoglobin fraction in the total amount of hemoglobin is noted $\alpha_{BL} = [HbO_2]/([HbO_2]+[Hb])$ and is commonly known as the blood oxygen saturation.

The absorption due to the presence of water and lipid in the measured tissue is defined as:

$$\mu_a^{WL}(\lambda) = \alpha_{WL}\mu_a^{Lipid}(\lambda) + (1-\alpha_{WL})\mu_a^{H2O}(\lambda)[\text{cm}^{-1}] \quad \text{(Eq.6)}$$

In this case the concentration of lipid related to the total concentration of lipid and water together can be written as $\alpha_{WF} = [\text{Lipid}]/([\text{Lipid}]+[H_2O])$, where [Lipid] and [$H_2O$], correspond to the concentration of lipid (density of 0.86 g/ml) and water, respectively.

This way of relating the water and lipid parameters in the expression of the absorption coefficient defined in Eq.6, rather than estimating separately the water and lipid volume fraction corresponds to a minimization of the covariance of the basic functions for fitting resulting in a more stable fit cf. the reference [R. Nachabé, B. H. W. Hendriks, M. V. D. Voort, A. E, and H. J. C. M. Sterenborg, "Estimation of biological chromophores using diffuse optical spectroscopy: benefit of extending the UV-VIS wavelength range to include 1000 to 1600 nm," Optics Express, vol. 18, 2010, pp. 879-888]. For further explanation and validation of this theorem reference is made to [R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm," Journal of Biomedical Optics, vol. 15, May. 2010, pp. 037015-10], which is hereby included by reference in entirety.

Another way to discriminate differences in spectra is by making use of a principal components analysis. This method allows classification of differences in spectra and thus allows discrimination between tissues. It is also possible to extract features from the spectra.

Figure 13:
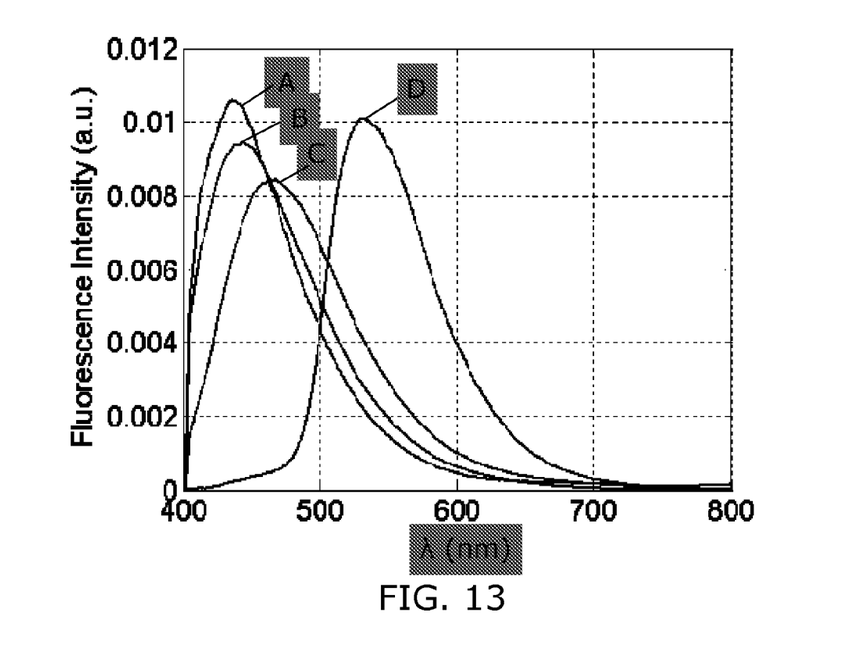
FIG. 13 illustrates a graph showing intrinsic fluorescence curves for A: collagen, B: elastin, C: NADH, and D: FAD.

FIG. 13 shows intrinsic fluorescence curves for A: Collagen, B: Elastin, C: NADH, and D: FAD. Such parameters could also be measured with a probe. Especially, the ratio NADH/FAD, which is called the optical redox parameter, could be calculated, since this ratio is an indicator for the metabolic state of the tissue, which is assumed to change upon effective treatment of cancer cells, see e.g. [Q. Zhang, M. G. Mueller, J. Wu and M. S. Feld, "Turbidity-free fluorescence spectroscopy of biological tissue" Opt. Lett. 25 (2000) p1451].

To sum up, the invention provides an interventional device, e.g. a Vacuum Assisted Biopsy (VAB) needle, incorporating optical fibers such that biological tissue in a volume at a side of the interventional device can be substantially completely optically probed by optical spectroscopy. In a VAB embodiment, a plurality of optical fiber pairs connected to respective optical ports, are placed at opposite positions along the suction cavity, and they are readout subsequently allowing to make a map of the tissue properties along the place where the tissue will be cut by the VAB needle. Based on decision software in an optical console, it can be determined whether the tissue present in the cutting cavity is completely normal tissue or not, prior to actually performing the biopsy on the tissue. In this way a well defined end point for VAB is created. In one embodiment, the optical fibers are arranged in a wall structure of a thin sleeve which fits onto existing VAB needles, thus allowing the VAB needle to be upgraded with an optical probing capability.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:
1. An interventional device comprising
a needle structure arranged for being inserted into biological tissue, the needle structure having a cavity positioned to a side of the needle structure and
a plurality of optical fibers externally accessible in one end and connected to optical ports in their opposite end, wherein the optical ports are spatially distributed on surface portions of the needle structure on opposite sides of the cavity, in order to allow optical probing of biological tissue present in the cavity, upon application of an optical signal to one of the plurality of optical fibers at a first side of the cavity and detection of an optical response thereto at another one of the plurality of optical fibers at the opposite side of the cavity.
2. Interventional device comprising
a needle structure arranged for being inserted into biological tissue, the needle structure having a cavity positioned to a side of the needle structure and
a plurality of optical fibers externally accessible in one end and connected to optical ports in their opposite end, wherein the optical ports are spatially distributed on surface portions of the needle structure on opposite sides of the cavity, in order to allow optical probing of biological tissue present in the cavity, upon application of an optical signal to one of the plurality of optical fibers at a first side of the cavity and detection of an optical response thereto at another one of the plurality of optical fibers at the opposite side of the cavity,
wherein the needle structure comprises a sleeve with a wall forming the cavity as a hollow space, and wherein the plurality of optical fibers are arranged at least partly within a structure of the wall of the cavity.

3. Interventional device according to claim 2, wherein at least a first optical port is arranged at a surface part of the wall, so as to direct light outside the sleeve in a direction perpendicular to a longitudinal extension of the sleeve, upon application of an optical signal, and wherein at least a second optical port is arranged at another surface part of the wall, so as to allow receipt of an optical response to said light from biological tissue present in the cavity positioned to a side of the sleeve.

4. Interventional device according to claim 3, wherein said at least first optical port is connected to an optical fiber) arranged within a structure of the wall of the sleeve following at least a part of a helical pattern, so that a vector along said optical fiber points outside the sleeve at said at least first optical port.

5. Interventional device according to claim2, wherein the optical ports are spatially distributed so as to cover different longitudinal positions of the cavity.

6. Interventional device according to claim 2, comprising a biopsy device,
wherein the structure of the biopsy device is arranged for being inserted into biological tissue and for taking a biopt thereof, wherein the cavity is configured so that a part of the biological tissue can be sucked upon application of a negative pressure, wherein the needle structure comprises a hole through which the biopt can be sucked upon application of a negative pressure, and
wherein the optical ports are spatially distributed so as to cover different longitudinal positions of the cavity, in order to allow optical probing of biological tissue present in the cavity, upon application of an optical signal to one of the plurality of optical fibers and detection of an optical response thereto at another one of the plurality of optical fibers.

7. Interventional device according to claim 6, wherein a plurality of optical ports are positioned along the cavity so as to allow optical probing of a total volume of biological tissue present in the cavity.

8. Interventional device according to claim 2, wherein the optical fibers are arranged in a wall of an obturator of the needle structure, along an axis of rotation of the needle geometry.

9. Interventional device according to claim 2, wherein the optical ports are formed as respective openings in a wall of an obturator) of the needle structure.

10. Interventional device according to claim 2, wherein the optical ports are formed as openings sealed by one of: an optically transparent resin, an optically scattering resin.

11. Interventional device according to claim 2, wherein a plurality of optical ports are arranged on a first straight line parallel with a longitudinal axis of the needle structure, and wherein a plurality of optical ports are arranged on a second straight line parallel with the first line.

12. Interventional device according to claim 2, comprising a console with at least one light source and a light detector, wherein the console is arranged for connection to the optical fibers, so as to allow emission of an optical signal from the light source to a first selection of the optical ports, and to allow receipt of light from a second selection of the optical ports.

13. Interventional device according to claim 2, comprising a console with at least one light source and a light detector, wherein the console is arranged for connection to the optical fibers, so as to allow emission of an optical signal from the light source to a first selection of the optical ports, and to allow receipt of light from a second selection of the optical ports,
wherein the console comprises a processor capable of determining respective measures of spectral contents of optical signals received from the second selection of the optical ports, and wherein the console is arranged to generate an output indicative of respective states of the biological tissue present at different longitudinal positions in the cavity of the needle structure accordingly.

* * * * *